(12) United States Patent
El Ghaouth et al.

(10) Patent No.: US 6,419,922 B1
(45) Date of Patent: Jul. 16, 2002

(54) *CANDIDA SAITOANA* COMPOSITIONS FOR BIOCONTROL OF PLANT POSTHARVEST DECAY

(75) Inventors: Ahmed El Ghaouth, Frederick, MD (US); Charles Wilson, Martinsburg, WV (US)

(73) Assignees: Biotechnology Research and Development Corporation, Peoria, IL (US); The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/324,525

(22) Filed: Jun. 2, 1999

Related U.S. Application Data

(60) Provisional application No. 60/088,300, filed on Jun. 5, 1998.

(51) Int. Cl.[7] ............................................. A61K 38/53
(52) U.S. Cl. ................................. 424/93.51; 424/94.6
(58) Field of Search ............................ 424/93.4, 93.51, 424/93.5, 93.1, 94.1, 94.6; 504/117

(56) References Cited

U.S. PATENT DOCUMENTS

| 5,591,429 A | 1/1997 | Wilson et al. ............ 424/93.51 |
| 5,633,025 A | 5/1997 | Ghaouth et al. .............. 426/62 |
| 5,670,368 A | 9/1997 | McLaughlin et al. ..... 435/255.5 |
| 5,830,459 A | * 11/1998 | Cuero ........................ 424/93.4 |

FOREIGN PATENT DOCUMENTS

| AU | WO 92/18009 | 10/1992 |
| EP | 646316 | * 4/1995 |
| JP | 60130346 | * 7/1985 |
| WO | 91/06313 | * 5/1991 |
| WO | WO 96/13985 | 5/1996 |

OTHER PUBLICATIONS

Mauch, F. et al (1988) "Anitfungal Hydrolases in Pea Tissue" *Plant Physiol* 88: 936–942.
Roberts, W.K. and Selitrennikoff, C.P. (1988) "Plant and Bacterial Chitinases Differ in Antifungal Activity" *J Gen Microbiol* 134:169–176.
Wilson, C.L. and Ghaouth, A. El (1993) "Multifaceted Biological of Postharvest Diseases of Fruits and Vegetables" *Amer Chem Soc* pp.: 181–185.
Allan, C.R. and Hadwiger, L.A. (1997) "The Fungicidal Effect of Chitosan on Fungi of Varying Cell Wall Composition" *Exp Mycol* 3: 285–287.

Droby, S. et al (1987) "Influence of $CaCl_2$ on *Penicillium digitatum*, Grapefruit Peel Tissue, and Biocontrol Activity of Pichia guilliermondii" *Phytopath* 87(3): 310–315.
Düring, K. (1993) "Can Lysozymes Mediate Antibacterial Resistance in Plants?" Plant Mol Biol 23: 209–214.
Freeman, A. and Dror Y. (1994) "Immobilization of 'Disguised' Yeast in Chemically Crosslinked Chitosan Beads" *Biotech and Bioengin* 44: 1083–1088.
Ghaouth, A. El et al. (1991) "Chitosan Coating Effect on Storability and Quality of Fresh Strawberries" *J Food Sci* 56(6): 1618–1620.
Ghaouth, A. El et al (1992) "Antifungal Activity of Chitosan on Post–Harvest Pathogens: Induction of Morphological and Cytological Alternations in *Rhizopus stolonifer*" *Mycol Res* 96(9): 769–779.
Ghaouth, A. El et al (1992) "Chitosan Coating to Extend the Storage Life of Tomatoes" *Hort Sci* 27(9): 1016–1018.
Manocha, M.S. and Govindsamy, V. (1997) "Chitinolytic Enzymes of Fungi and Their Involvement in Biocontrol of Plant Pathogens" *Plant–Microbe Interactions and Biological Control* Marcel Dekker, Inc. New York.
Wisniewski et al., Physiol Mol Plant Pathol, (1991) 39 (4), 245–258.*
Castoria et al., 1997, Postharvest Biol. Technol., 12:293–300.*
Arras et al., 1996, Postharvest Biol. Technol., 8:191–198.*
Droby et al., In Biological control of Postharvest Diseases— Theory and Pracie, CRC Press, Wilson et al., Ed., pp. 63–75.(1994).*
Gordee,et al., New Approaches Antifungal Drugs (1992), 46–63. Editor(s): Fernandes, Prabhavathi B. Publisher: Birkhaeuser, Boston, Mass.*

* cited by examiner

*Primary Examiner*—Irene Marx
(74) *Attorney, Agent, or Firm*—Barnes & Thornburg; Alice O. Martin

(57) ABSTRACT

Novel methods and compositions are provided for the biocontrol of plant diseases, in particular diseases causing plant postharvest decay. The novel compositions are "biocontrol cocktails" that are combinations of antagonistic microorganisms and antifungal agents. Suitable microorganisms include yeasts such as Candida spp. Suitable antifungal agents include enzymes or combinations of enzymes such as lysozyme or lyticase. The compositions are applied to the plants either to prevent or cure infections caused by microorganisms such as fungi. Synergistic effects occur. The methods and compositions are comparable to or better than synthetic fungicides or to either agent alone.

1 Claim, No Drawings

CANDIDA SAITOANA COMPOSITIONS FOR BIOCONTROL OF PLANT POSTHARVEST DECAY

This application claims priority from U.S. Provisional Application Ser. No. 60/088,300 which was filed on Jun. 5, 1998, now abandoned.

Novel methods and compositions are provided for the biocontrol of plant diseases, in particular diseases causing postharvest decay. The methods and compositions are both protective and curative. Combinations of antagonistic microorganisms and antifungal agents are used.

BACKGROUND OF THE INVENTION

The U.S. market for biocontrol of tree fruit postharvest diseases could exceed $100 million by the year 2000 (*Industrial Bioprocessing*, September 1992). In *Postharvest News and Information* (1991) it was estimated that approximately 25% of harvested fruit and vegetables are lost because of postharvest diseases. Synthetic fingicides have been the primary means for controlling postharvest diseases of fruit and vegetables. However, increased concern of the public over the carcinogenicity of synthetic fungicides, has led to the withdrawal of some fungicides from the market. The development of fungicide-resistance in pathogens has limited chemical fingicides as a means of controlling them.

Control of plant diseases is not a problem confined to the U.S. The European Parliament has voted in favor of a total ban on postharvest treatment of fruit and vegetables with pesticides as soon as this ban becomes feasible. The withdrawal of current fungicides from use in the United States and other parts of the world is creating a large, new market for biological control agents ("biocontrol"). Baker (1987) has defined biological control as "the decrease of inoculum or the disease-producing activity of a pathogen accomplished through one or more organisms, including the host plant but excluding man." The cost of commercializing a biological control agent is much less expensive than the cost of commercializing a synthetic pesticide because only Tier 1 toxicology tests (Hofstein et al 1994.) are required. Also, if a biological control agent is properly selected, fewer new environmental impact studies are required.

A type of biological control agent is a microorganism that is antagonistic to postharvest pathogens. For example, antagonistic yeasts have been disclosed as effective biocontrol agents for the biological control of postharvest disease (Wilson and El Ghaouth, 1993, 1997). However, microorganisms currently available have not been accepted as providing control comparable to control obtained by the use of synthetic fungicides. Some limitations are due to the microorganisms'inability to cure previously-established infections in the crops and to prevent the resumption of quiescent infections. Improved and broader biocontrol is desirable.

Antifungal hydrolases such as chitinase, $\beta$-1,3-glucanase, lysozyme, and lyticase are low molecular proteins that hydrolyze the main components of fungal and yeast cell walls, $\beta$-glucan and chitin (Bowles, 1990; Mauch et al., 1988; Schlumbaum et al, 1986; Kendra et al., 1989; Sahai and Manocha, 1993). These enzymes are reported to play a major role in disease resistance of plants against invading pathogens and may be responsible for the biocontrol activity of some microbial antagonists. The action of glucanohydrolases was reported to inhibit fungal growth (Schlumbaum et al., 1986; Sela-Buurlage et al., 1993).

New means of controlling postharvest diseases are needed that are safe, effective, and economically feasible. The present invention provides such means.

SUMMARY OF THE INVENTION

The present invention is directed to novel compositions that are combinations of antagonistic microorganisms with antifungal agents, and to methods of preventing or curing plant diseases caused by various postharvest pathogens that cause decay of plants by applying the compositions of the present invention to plants. "Prevention or curing" is included under the general term "biocontrol" of plants. Percent of plants infected is a measure of control. Postharvest decay is one of the detrimental phenomena that is controlled by methods and compositions of the present invention.

The combinations of the present invention form a "biocontrol cocktail." Suitable antagonistic yeasts include those from the following genera: Candida spp; Cryptococcus spp; Pichia spp; Debaryomyces spp; Bulleromyces spp; Sporobolomyces spp; Rhodotorula spp; Aureobasidium spp; Issatchenkia spp; Zygosaccharomyces spp; Dekkera spp; and Hansenula spp. Other suitable microorganisms include bacteria, for example *Pseudomonas syringae* and *Bacillus subtilus*. Suitable enzymes and biochemicals include the enzymes chitinase, laminarase, chitosanase, $\beta$-1,3-glucanase, lectins; and the biochemicals: $\beta$-1,3-glucan, $\beta$-1,4-glucan, a polysaccharide of fungal or yeast origin, and polycations such as glycoprotein.

In a preferred embodiment of a composition of the present invention, the antagonistic microorganism is a yeast and the antifungal agent is an enzyme. For example, the combination of the antifungal property of an enzyme, e.g., lysozyme and/or lyticase and the biocontrol activity of an antagonistic yeast, e.g., *C. saitoana*, wherein the yeast can function against the pathogen in the presence of the enzymes, provides improved consistency and efficacy in controlling postharvest rot (decay). In addition, the combination of antagonistic yeast (*C. saitoana*) with lysozyme or lyticase offers control of postharvest decay of fruit and vegetables superior to that obtained with an antagonist yeast alone or with an enzyme alone such as lysozyme or lyticase. This improvement and synergism is unexpected.

The combination of antagonistic microorganisms such as a yeast with antifungal enzymes (lysozyme or lyticase) was not expected to successfully work to effect biocontrol of plant pathogens or to produce a synergistic effect because of the known actions of each agent individually. Antifungal hydrolases such as chitinase, $\beta$-1,3-glucanase, lysozyme, and lyticase are known to hydrolyze the main components of fungal and yeast cell walls, $\beta$-glucan and chitin, and thereby negatively affect the growth of the yeasts such as Candida spp. and of filamentous fungi. Therefore, a combination of an antagonist yeast with antifungal enzymes was expected to impair the biocontrol activity of the selected yeast. However, unexpectedly, the combination produced improved control of pathogens.

Compositions including antagonistic microorganisms such as a yeast (*C. saitoana*) with antifungal agents such as the enzymes lysozyme or lyticase may be applied to plants either before or after infection because the compositions have both a protective and a curative effect against major postharvest pathogens and consequently offer a level of control of decay better than that of synthetic chemical fingicides.

It is contemplated that a plurality of antagonistic microorganisms may be combined, as long as the microorganisms do not adversely affect the antagonism, viability, or other parameters that are needed for antagonistic microorganism activity according to the present invention. In addition, not only may a plurality of microorganisms be effective in combination with one antifungal agent, but a plurality of antifungal agents may also be effective, provided the plurality of antifungal agents do not deleteriously affect the biocontrol action either of other agents or microorganisms combined with them.

The compositions of the present invention are applied to plants by means such as spraying, drenching, or dipping, which are known in the art. Effective amounts of antifungal agents, e.g. enzymes, have been found to range from 20 µg/ml to about 1000 µg/ml, with about 100 µg/ml being preferred. Effective amounts of yeasts have been found to range from about $10^6$ CFU to about $10^8$ CFU with $10^8$ CFU preferred. It is understood, however, that optimal concentrations will vary with particular situations, and it is well within the level of skill in the art to arrive at optimal formulations by following conventional testing procedures such as those described by the Examples herein.

The complexity of the mode of action displayed by the combined agents of the present invention makes the development of pathogen resistance in the target plants more difficult to achieve and presents a highly complex disease deterrent barrier.

The combination of antagonistic microorganisms with antifungal biochemicals provides effective control against the major rots affecting agricultural commodities such as pome fruits, citrus fruits, vegetables, root crops, stone fruits, tropical fruits, tomato, and other plants.

DETAILED DESCRIPTION OF THE INVENTION

"Biocontrol cocktails" are compositions of the present invention that are combinations of microorganisms antagonistic to postharvest pathogens that deleteriously affect agricultural commodities, with antifungal agents. The present invention provides a biological protective effect as well as a curative effect.

Fruits and plants that are targets for the methods and compositions of the present invention include pome fruit (e.g., apple, pear); stone fruit (e.g., peach, nectarine, prune); citrus fruit (e.g., orange, lemon, grapefruit, tangerine); root crops (carrots, potato); vegetables (e.g., tomato, bell pepper, cucumber); tropical fruit (e.g., mango, banana, guava, pineapple, avocado); and melon fruit.

An embodiment of the invention is a composition including antagonistic yeasts with antifungal enzymes. Among the enzymes suitable for practice of the invention, hydrolases such as lysozyme and lyticase were found to significantly increase the biological activity of antagonistic yeasts such as C. saitoana that was reported by Wilson and El Ghaouth in U.S. Pat. No. 5,591,429, incorporated herein by reference. Combining yeast with an enzyme exerted an unexpected synergistic biocontrol effect. This combination makes it possible to exploit the biological property of antifungal enzymes and the biocontrol activity of a microbial antagonist. Although antifungal enzymes such as lysozyme and lyticase are inhibitory to postharvest pathogens such as Botrytis cinerea (Table 1), they show no effect on the growth of the yeast C. saitoana (Table 2). Therefore, these ingredients may be combined and the yeast biocontrol activity will be maintained.

Unexpectedly, the combination of antagonistic yeast with lysozyme or lyticase was more effective in controlling infection of apple and citrus than either the antagonist or the enzyme alone (Tables 3 and 4). Increasing the concentration of lysozyme from 100 to 1000 µg/ml resulted in an increase in the effectiveness of the combination (Table 3). In the test conducted with orange fruit, only 30% and 26% of fruit treated with the combination of C. saitoana with lysozyme or lyticase were infected, while 88%, 88%, and 58% of the fruit treated with lysozyme, lyticase, or C. saitoana alone were diseased. All of the control fruit were diseased (Table 4). The same pattern of decay control by the combination was also observed in apple and lemon fruit. (Tables 3 and 4)

In addition to having a protective effect, the compositions of the present invention, e.g. combination of antagonistic yeast with lysozyme or lyticase, also displayed a curative activity against major postharvest pathogens, e.g. apple and citrus fruit (Table 5). The combination of C. saitoana with lysozyme was effective in controlling decay of orange and lemon fruit due to natural infection. The level of disease control obtained with the combination was comparable to that obtained with the recommended fungicide Imazalil (Fungaflor 500EC, 44.6% active ingredient, Janssen Pharmaceutica, Titusville, N.J.). (Table 6).

EXAMPLES

The following examples illustrate some of the embodiments of the invention:

Example 1

Effect of an Antifungal Enzyme Alone on the Growth of Postharvest Disease Pathogens and on Yeast The inhibitory activity of antifungal enzymes, in this example, lysozyme and lyticase, against the pathogen Botrytis cinerea, was determined in a 24-well microtiter dish. Autoclaved solutions of 0.2% maltose extract broth were amended with membrane-sterilized solutions of lysozyme and lyticase to obtain a concentration of 0.1% and 0.5% of lysozyme and lyticase, respectively. One hundred microliters of the enzyme solution was dispensed into each well. Each well was inoculated with five hundred spores of B. cinerea. Four replicates of eight wells were used for each treatment. Microtiter dishes were incubated in the dark at 24° C. Percent spore germination was determined after 24 hours. The results are shown in Table 1. Spores were inhibited by either enzyme.

The effect of lysozyme and lyticase on the survival of C. saitoana in yeast maltose broth was also determined. Culture flasks containing sterile solutions of 0.2% yeast maltose broth were amended with membrane-sterilized solutions of lysozyme and lyticase to obtain a concentration of 0.1% and 0.6% of lysozyme and lyticase, respectively. Each flask was started with approximately $10^4$ colony forming units (CFU) of yeast and the flasks were incubated on an orbital shaker set at 200 rpm. Samples were collected and dilution-plated in duplicate on yeast-maltose agar medium. The plates were incubated 24° C. and colonies were counted after 48 h. Table 2 shows there was no effect on survival of yeast treated with the enzymes.

Example 2

Protective and Curative Biocontrol Activity of the Combination of Antifungal Enzymes with Yeast Yeast cells from 48 hour old cultures of C. saitoana were pelleted by centrifugation, resuspended in sterile distilled water, and centrifuged. Pellets were suspended in water, 0.01% and 0.1% lysozyme of 0.6% lyticase, and the concentration of the yeast suspension was adjusted to $10^8$ CFU/ml.

Apple, orange, and lemon fruit were individually wounded and each wound was treated with fifty microliters of one of the following treatments:

control sterile water;

yeast cell suspension (*C. saitoana*);

yeast cell suspension containing 0.01% or 0.1% lysozyme;

yeast cell suspension containing 0.6% lyticase;

0.01% or 0.1% lysozyme;

0.6% lyticase.

Fruit wounds were either treated with the different treatments and then inoculated with 20 μL of a pathogen spore suspension to determine protective effects, or inoculated with a pathogen spore suspension and 24 hours later were treated with the different treatments to determine curative effects. Apple wounds were inoculated (i.e., pathogens were placed in the wound) with the pathogens *B. cinerea* and *P. expansum*, whereas orange and lemon wounds were inoculated with *P. digitatum*. Treated fruit were incubated at 24° C. in plastic trays at high humidity. For each treatment, 20 to 100 fruit were arranged in a randomized complete block design. Percent infection was determined for each treatment after 7 days of storage. The tests were repeated twice. Results of the protective effects on apple fruit decay are shown in Table 3. The greatest degree of protection was shown by treatment of 0.1% lysozyme and *C. saitoana*. Control of decay of oranges and lemons was most effective using either 0.01% lysozyme or 0.1% lyticase and yeast (Table 4). The effect was greater than for either agent alone.

In the past, the lack of curative activity has been identified as a major limitation of biological approaches to pathogen control. Indeed, treatment of apple and citrus fruit with either *C. saitoana*, lysozyme, and lyticase had little effect on established infection caused by *P. expansum* and *P. digitatum* (Table 5), than the combination of antagonistic yeast with lysozyme or lyticase which was very effective in controlling infections that occurred 24 hours prior to the application of the treatment. The observed curative activity of the combination demonstrated the synergy between the antagonist and the antifungal enzyme (lysozyme or lyticase).

Additional tests were also done to determine the effect of different combinations of biochemicals and microorganisms on natural infections of citrus fruit. Orange and lemon fruit from field bins were washed on line following standard commercial practices [Standard Pre Chlorine was (50 ppm); size and color blemish sorting, and randomized]. Thereafter the fruit was washed and treated with either water, a yeast cell suspension containing 0.1% lysozyme, or Imazalil using an on line spray system. Each treatment consisted of at least 8 to 13 boxes of fruit; each box representing a replicate of approximately 60 to 100 fruit. The fruit was held at 50–55° F. and the percentage of decay was determined after 3 weeks. Results are shown in Table 6.

TABLE 1

Effect of Lysozyme and Lyticase on Spore Germination.

| Treatment[a] | Inhibition of Germination (%) *Botrytis cinerea* |
|---|---|
| Maltose extract broth (MEB) | 0 |
| 0.1% lysozyme + MEB | 100 |
| 0.6% lyticase + MEB | 100 |

[a]Microtiter wells containing lysozyme and lyticase solutions amended with 0.2% maltose extract broth were inoculated with five hundred spores of *Botrytis cinerea* and the microtiter dish was incubated at 24° C. Spore germination was determined after 24 hours.

TABLE 2

Survival of *Candida saitoana* in Different Enzyme Solutions.

| | Yeast Cell Counts (CFU/ml) | |
|---|---|---|
| Treatment[b] | 1 day | 4 days |
| Yeast maltose broth (YMB) | >2.0 × 10$^5$ | >2.0 × 10$^5$ |
| 0.1% lysozyme + YMB | >2.0 × 10$^5$ | >2.0 × 10$^5$ |
| 0.6% lyticase + YMB | >2.0 × 10$^5$ | >2.0 × 10$^5$ |

[b]Lysozyme and lyticase solutions amended with yeast maltose broth were inoculated with 10$^4$ yeast cells/ml and the solutions were stored at room temperature. Yeast survival was determined at different times over a period of 4 days.

TABLE 3

Protective Effect of the Combination of *Candida saitoana* with Different Concentrations of Lysozyme on Decay of Apple Fruit Caused by *Botrytis cinera*.

| Treatment[c] | Infected Fruit (%)[d] *Botrytis cinerea* |
|---|---|
| Control | 100a |
| 0.01% lysozyme | 100a |
| 0.1% lysozyme | 100a |
| *C. saitoana* | 32b |
| 0.01% lysozyme + *C. saitoana* | 35b |
| 0.1% lysozyme + *C. saitoana* | 17c |

[c]Apple wounds were treated with the different treatments and then challenge inoculated with 20 μL of *B. cinerea* at 10$^5$ conidia/ml. Fruits were evaluated for symptoms of decay after 18 days of storage at 24° C.
[d]Columns with the same letter are not significantly different according to Duncan's multiple range test (P = 0.5). Those with different letters show significant differences (Steele and Torrie, 1960).

TABLE 4

Protective Effect of the Combination of *Candida saitoana* with Lysozyme or Lyticase on Decay of Orange and Lemon Fruit Caused by *Penicillium digitatum*.

| | Infected Fruit (%)[f] *Penicillium digitatum* | |
|---|---|---|
| Treatment[e] | Lemon | Orange |
| Control | 100a | 100a |
| 0.01% lysozyme | 86b | 88b |
| 0.1% lyticase | 85b | 88b |
| *C. saitoana* | 53c | 58c |
| 0.01% lysozyme + *C. saitoana* | 21d | 30d |
| 0.1% lyticase + *C. saitoana* | 15d | 26d |

[e]Orange and lemon fruits were wounded and immediately afterward wounds were treated with the different treatments. Treated wounds were challenge inoculated with 20 μL of *P. digitatum* at 10$^4$ conidia/ml. Fruits were evaluated for symptoms of decay after 7 days of storage at 24° C.
[f]Columns with the same letter are not significantly different according to Duncan's multiple range test (P = 0.5).

TABLE 5

Curative Effect of the Combination of *Candida saitoana* with Lysozyme or Lyticase on Decay of Apple, Orange and Lemon Fruit.

| | Infected Fruit (%)[h] | | |
|---|---|---|---|
| Treatment[g] | Apple | Lemon | Orange |
| Control | 56a | 100a | 100a |
| *C. saitoana* | 78b | 97a | 96a |
| 0.1% lysozyme | 33c | 82b | 79b |

TABLE 5-continued

Curative Effect of the Combination of *Candida saitoana* with Lysozyme or Lyticase on Decay of Apple, Orange and Lemon Fruit.

| | Infected Fruit (%)[h] | | |
|---|---|---|---|
| Treatment[g] | Apple | Lemon | Orange |
| 0.6% lyticase | 22d | 77b | 74b |
| 0.1% lysozyme + *C. saitoana* | 33c | 27c | 32c |
| 0.6% lyticase + *C. saitoana* | 11e | 32c | 23 |

[g]Apple wounds were inoculated with spore suspensions of *P. expansum*, while orange and lemon wounds were challenge inoculated with *P. digitatum*. After 24 hours incubation at 24° C., inoculated wounds were treated with 50 μL of $10^8$ CFU/ml of yeast cells (strains *C. saitoana*) suspended in sterile water. 0.1% lysozyme, or lyticase. Fruits were evaluated for symptoms of decay after 7 days of storage at 24° C.
[h]Columns with the same letter are not significantly different according to Duncan's multiple range test (P = 0.5).

TABLE 6

Effect of the Combination of *Candida saitoana* with Lysozyme on Natural Infection of Orange and Lemon Fruit.

| | Infected Fruit (%)[j] *Penicillium digitatum* | |
|---|---|---|
| Treatment[i] | Lemon | Orange |
| Control | 11.2a | 11.7a |
| 0.1% lysozyme + *C. saitoana* | 6.7b | 4.3b |
| Imazalil | 4.6b | 2.4b |

[i]Orange and lemon fruit were treated within 48 hours after harvest under semi-commercial conditions using a processing line. Fruit from field bins were washed on line following standard commercial practices and then treated with water, yeast cells (strains *C. saitoana*) suspension containing 0.1% lysozyme, or Imazalil using a line spray system. Each treatment consisted of 8 to 10 boxes of fruit; each box representing a replicate of 70 to 100 fruits. The percentage decay was determined after 3 weeks.
[j]Columns with the same letter are not significantly different according to Duncan's multiple range test (P = 0.5).

Materials and Methods

Preparation of Fruit

Ripe apples (cv. Red Delicious) were hand-harvested at the Appalachian Fruit Research Station, Kearneysville, W.Va. Orange (cv. Valencia or Navel) and lemon (cv. Eureka) fruit were purchased and stored at 4° C. The fruit was sorted to remove any fruit with apparent injuries or infections.

Preparation of Microorganisms Causative of Plant Disease

Cultures of *Botrytis (B.) cinerea, Penicillium (P.) expansum* Link, and *Penicillium (P.) digitatum* were maintained on potato dextrose agar (PDA). Spore suspensions of the cultures were obtained by flooding 2-week-old cultures of *B. cinerea, P. expansum* Link, and *P. digitatum* with sterile distilled water containing 0.1% (v/v) Tween 80. [Sigma Chemical Co., St. Louis, Mo.] Spore counts were determined with an hemacytometer, and spore concentration was adjusted with sterile distilled water.

Preparation of Yeast

The yeast *C. saitoana* was grown for 48 h at 27° C. Shake-flask cultures of nutrient-yeast broth were started with approximately $10^8$ CFU of yeast and incubated on an orbital shaker set at 200 rpm for 48 h. Yeast cells were collected by centrifugation at 3000 g for 20 min, resuspended in sterile distilled water, and centrifuged. The resulting pellets were dispersed in sterile distilled water and the concentration of the yeast suspension was adjusted to $10^8$ CFU/ml.

DOCUMENTS CITED

Baker, K. F. (1987), *Ann. Rev. Phytopathol.* 25:67–85.
Bowles, D. J. (1990), *Ann. Rev. Biochem.* 59:873–907.
During, K. (1993), *Plant MoL Biol.*, 23:209–214.
Hofstein, R. S., Droby, S., Chalutz, E., Friedlander, T. (1994) In: Wilson, C. L., Wisniewski, M. E. (eds.) *Biological Control of Postharvest Diseases of Fruits and Vegetables.* CRC Press, pp. 89–100.
*Industrial Bioprocessing* (September, 1992).
Kendra, F. D., Christian, D. and Haldwiger, L. A. (1989), *Physiol. and Mol. Plant Path.*, 32:215.
Mauch, F., Mauch-Mani B. and Boller T. (1988), *Plant Physiol.*, 88:936–942. *Postharvest News & Information* (1991).
Sahai, A. S., and Manocha, M. S. (1993), *FEMS Microbiology Reviews*, 11:317–339.
Schlumbaum, A., Mauch, F., Vogeli, U., and Boller, T. (1986), *Nature*, 324:365.
Sela-Buurlage, M. B., Ponstein, A. S., Bres-Vloemans, B., Melchers, L. O., Van den Elzen, P., Cornelissen, B. J. C. (1993), *Plant Physiol.*, 101:857–863.
Steele, R. D. and Torrie, J. H. (1960) *Principles and Procedures of Statistics*, McGraw-Hill, New York, N.Y.
Wilson, C. L. and El Ghaouth, A. (1993) *Symposium Proceeding. Beltsville Symposium XVIII*, American Chemical Society.
Wilson, C. L. and El Ghaouth, A., U.S. Pat. No. 5,591,429 (1997).

We claim:

1. A composition for biocontrol of diseases on plants, said composition consisting essentially of *C. saitoana*, a yeast antagonistic to plant pathogens to which is added an antifungal agent that is a hydrolase selected from the group consisting of lysozyme and lyticase in an amount sufficient to effect biocontrol of diseases on plants.

* * * * *